United States Patent
Bleicher et al.

(10) Patent No.: US 11,390,641 B2
(45) Date of Patent: Jul. 19, 2022

(54) 5'S-LNA NUCLEOTIDES AND OLIGONUCLEOTIDES

(71) Applicant: Hoffmann-La Roche Inc., Little Falls, NJ (US)

(72) Inventors: Konrad Bleicher, Basel (CH); Joerg Duschmalé, Basel (CH); Goutam Saha, Kolkata (IN); Juber Abdulhamid Shaikh, Hinjewadi MIDC (IN)

(73) Assignee: Hoffmann-La Roche Inc., Little Falls, NJ (US)

( * ) Notice: Subject to any disclaimer, the term of this patent is extended or adjusted under 35 U.S.C. 154(b) by 562 days.

(21) Appl. No.: 16/317,586

(22) PCT Filed: Jul. 24, 2017

(86) PCT No.: PCT/EP2017/068575
§ 371 (c)(1),
(2) Date: Jan. 14, 2019

(87) PCT Pub. No.: WO2018/019748
PCT Pub. Date: Feb. 1, 2018

(65) Prior Publication Data
US 2019/0292213 A1     Sep. 26, 2019

(30) Foreign Application Priority Data

Jul. 27, 2016 (IN) .............................. 201641025669

(51) Int. Cl.
| | |
|---|---|
| *C07H 19/06* | (2006.01) |
| *A61K 31/7088* | (2006.01) |
| *C07H 1/00* | (2006.01) |
| *C07H 19/16* | (2006.01) |
| *C07H 21/00* | (2006.01) |
| *C12N 15/113* | (2010.01) |
| *C07H 5/10* | (2006.01) |
| *C07H 19/00* | (2006.01) |

(52) U.S. Cl.
CPC ......... *C07H 19/06* (2013.01); *A61K 31/7088* (2013.01); *C07H 1/00* (2013.01); *C07H 5/10* (2013.01); *C07H 19/00* (2013.01); *C07H 19/16* (2013.01); *C07H 21/00* (2013.01); *C12N 15/113* (2013.01); *C12N 2310/3231* (2013.01)

(58) Field of Classification Search
None
See application file for complete search history.

(56) References Cited

FOREIGN PATENT DOCUMENTS

| | | |
|---|---|---|
| CN | 1115320 | 1/1996 |
| JP | H10-503773 | 4/1998 |
| JP | 2005-500855 | 1/2005 |
| JP | 2007-523601 | 8/2007 |
| WO | WO 96/04295 | 2/1996 |
| WO | WO 03/018838 | 3/2003 |
| WO | WO 2016/017422 | 2/2016 |

OTHER PUBLICATIONS

Iyer, Current Protocols in Nucleic Acid Chemistry (2000) 2.1.1-2.1.17/ (Year: 2000).*
Cosstick, "Synthesis, Properties and Application of Nucleic Acids Containing Phosphorothiolate Linkages," Curr. Org. Chem., Mar. 2008, 12:291-308.
Das et al., "General acid catalysis by the hepatitis delta virus ribozyme," Nat Chem Biol., Jun. 2005, 1(1):45-52.
Eckstein, "Phosphorothioate oligodeoxynucleotides: what is their origin and what is unique about them?," Antisense and Nucleic Acid Drug Development, Apr. 2009, 10(2):117-21.
International Search Report and Written Opinion in International Application No. PCT/EP2017/068575, dated Nov. 3, 2017, 12 pages.
International Preliminary Report on Patentability in International Application No. PCT/EP2017/068575, dated Jan. 29, 2019, 8 pages.
Jahn-Hofmann et al., "Efficient Solid Phase Synthesis of Cleavable Oligodeoxynucleotides Based on a Novel Strategy for the Synthesis of 5'-S-(4,4'-Dimethoxytrityl)-2'-deoxy-5'-thionucleoside Phosphoramidites ," Helv Chim Acta., Nov. 24, 2004, 87(11):2812-2828.
Sharma et al., "Design and Synthesis of LNA-Based Mercaptoacetamido-Linked Nucleoside Dimers," Nucleosides, Nucleotides and Nucleic Acids., Jan. 1, 2013, 32(5):256-272.
Wei, "Coupling activators for the oligonucleotide synthesis via phosphoramidite approach," Tetrahedron, May 6, 2013, 69(18):3615-3637.
Zamecnik et al., "Inhibition of Rous sarcoma virus replication and cell transformation by a specific oligodeoxynucleotide," P Natl Acad Sci USA., Jan. 1978, 75(1):280-284.

* cited by examiner

*Primary Examiner* — Layla D Berry
(74) *Attorney, Agent, or Firm* — Fish & Richardson P.C.

(57) ABSTRACT

The invention relates to a compound of formula (I) wherein R2 and R4 are joined and together form a group, such a —CH2O—. The compound of formula (I) can be used in the manufacture of 5'S-LNA oligonucleotides as antisense drugs.

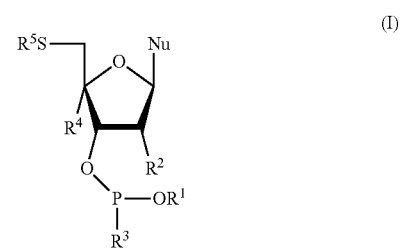

30 Claims, No Drawings

5'S-LNA NUCLEOTIDES AND OLIGONUCLEOTIDES

CROSS REFERENCE TO RELATED APPLICATIONS

This application is a National Phase application under 35 U.S.C. § 371 of PCT International Application number PCT/EP2017/068575 filed Jul. 24, 2017, which claims priority to IN201641025669 filed Jul. 27, 2016. The entire contents of the foregoing applications are hereby incorporated by reference.

The invention relates to a LNA phosphoramidite building block bearing a sulfur atom in the 5'-position of the sugar ring, to a process for the manufacture of this building block, and to a process for manufacturing an oligonucleotide comprising this building block.

The invention thus relates in particular to a compound of formula (I)

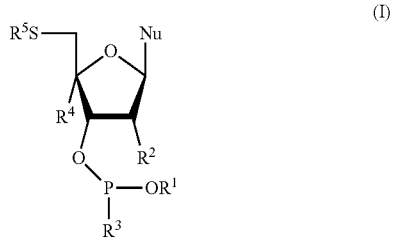

wherein
$R^1$ is a phosphate protecting group;
$R^2$ and $R^4$ together form —$CH_2O$—, —$CH_2NH$—, —$CH_2S$—, —$CH_2N(OR^P)$—, —$CHCH_3O$—, —$C(CH_3)_2O$—, —$CH_2C(=CH_2)$—, —$CHCH_3C(=CH_2)$—, —$CHCH_3S$—, —$CH_2NR^P$—, —$CH_2CH_2O$—, —$CH_2CH_2CH_2O$—, —$CH_2OCH_2$—, —$CH(CH_2OCH_3)O$—, —$CH(CH_2CH_3)O$— or —$CH_2OCH_2O$—;
$R^3$ is dialkylamino;
$R^5$ is a thiohydroxyl protecting group;
each $R^P$ is alkyl; and
Nu is a nucleobase optionaly comprising a protected primary amino group.

The use of oligodeoxynucleotides as therapeutic agents, where the well-understood principles of Watson-Crick hybridization are exploited to target complementary RNA strands, has witnessed remarkable progress since its inception in the late 1970's (P. C. Zamecnik, M. L. Stephenson, *P Natl Acad Sci USA* 1978, 75, 280-284; S. T. Crooke, *Antisense drug technology: principles, strategies, and applications*, 2nd ed. ed., Boca Raton, Fla.: CRC Press, 2008).

Several types of chemical modifications have been introduced over time in synthetic oligonucleotides in order to e.g. extend their half-life, improve pharmacokinetics, enhance the RNaseH activity, reduce toxicity or enhance mismatch discrimination.

One of the most successful modifications is the introduction of phosphorothioate linkages, where one of the non-bridging phosphate oxygen atoms is replaced with a sulfur atom (F. Eckstein, *Antisense and Nucleic Acid Drug Development* 2009, 10, 117-121). Such phosphorothioate oligodeoxynucleotides show an increased protein binding as well as a distinctly higher stability to nucleolytic degradation and thus a substantially higher half-life in plasma, tissues and cells than their unmodified phosphodiester analogues. This allowed the development of the first generation of oligonucleotide therapeutics and opened the door of the later generation modifications such as Locked Nucleic Acids (LNAs).

Replacement of a phosphodiester linkage with a phosphorothioate, however, creates a chiral center at the phosphorous atom. As a consequence, all approved oligonucleotide therapeutics are until now mixtures of a huge amount of diastereoisomeric compounds, with potentially different (and possibly opposing) physiochemical properties.

In order to reduce the diastereoisomeric complexity of such oligodeoxynucleotides, the sulfur atom within a phosphorothioate can in theory be shifted from one of the nonbridging positions to the bridging 5'-position of the ribose sugar. This modification renders the substitution pattern around the phosphorous symmetrical and thus removes the chiral center, consequently reducing the diastereoisomeric complexity of the molecule.

Oligonucleotides containing such 2',5'-dideoxy-5-mercapto building blocks have been prepared (see R. Cosstick, J. Gaynor, *Curr. Org. Chem.* 2008, 12, 291-308 and references therein) and examined in diverse contexts such as for example site specific cleavage (e.g. K. Jahn-Hofmann, J. W. Engels, *Helv. Chim. Acta* 2004, 87, 2812-2828) or mechanistic investigations in chemical biology (e.g. S. R. Das, J. A. Piccirilli, *Nat Chem Biol* 2005, 1, 45-52). Their application in a therapeutic context especially with the intent of reducing the diastereoisomeric complexity of phosphorothioate oligonucleotides, however, has received far less attention. Furthermore, the combination of such a 2',5'-dideoxy-5'-mercapto modification with a Locked Nucleic Acid (LNA) sugar moiety is completely unprecedented.

We have surprisingly found a process that gave access for the first time to LNA phosphoramidite building blocks bearing a sulfur atom in the 5'-position of the sugar ring and applied them to the synthesis of modified oligonucleotides. The invention thus provides an entry into such 5'-mercapto modified LNAs. When included into oligonucleotides, it reduces the diastereomeric complexity of the resulting molecule.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 3 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, propyl and isopropyl.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy. Particular "alkoxy" are methoxy and ethoxy.

The term "halogen" or "halo", alone or in combination, signifies fluorine, chlorine, bromine or iodine and particularly chlorine, bromine or iodine. The term "halo", in combination with another group, denotes the substitution of said group with at least one halogen, particularly substituted with one to five halogens, particularly one to four halogens, i.e. one, two, three or four halogens.

The term "aryl", alone or in combination, signifies the phenyl or naphthyl group.

The terms "hydroxyl" and "hydroxy", alone or in combination, signify the —OH group.

The terms "thiohydroxyl" and "thiohydroxy", alone or in combination, signify the —SH group.

The term "amino", alone or in combination, signifies the primary amino group (—$NH_2$), the secondary amino group (—NH—), or the tertiary amino group (—N—).

The term "oxy", alone or in combination, signifies the —O— group.

The term "protecting group", alone or in combination, signifies a group introduced into a molecule by chemical modification of a functional group to obtain chemoselectivity in a subsequent chemical reaction.

"Phosphate protecting group" is a protecting group of the phosphate group. Examples of phosphate protecting group are 2-cyanoethyl and methyl. A particular example of phosphate protecting group is 2-cyanoethyl.

"Hydroxyl protecting group" is a protecting group of the hydroxyl group. Examples of hydroxyl protecting groups are acetyl (Ac), benzoyl (Bz), benzyl (Bn), β-methoxyethoxymethyl ether (MEM), dimethoxytrityl (or bis-(4-methoxyphenyl)phenylmethyl) (DMT), trimethoxytrityl (or tris-(4-methoxyphenyl)phenylmethyl) (TMT), methoxymethyl ether (MOM), methoxytrityl [(4-methoxyphenyl)diphenylmethyl (MMT), p-methoxybenzyl ether (PMB), methylthiomethyl ether, pivaloyl (Piv), tetrahydropyranyl (THP), tetrahydrofuran (THF), trityl or triphenylmethyl (Tr), silyl ether (for example trimethylsilyl (TMS), tert-butyldimethylsilyl (TBDMS), tri-iso-propylsilyloxymethyl (TOM) and triisopropylsilyl (TIPS) ethers), methyl ethers and ethoxyethyl ethers (EE). Particular examples of hydroxyl protecting group are DMT and TMT, in particular DMT.

"Thiohydroxyl protecting group" is a protecting group of the thiohydroxyl group. Examples of thiohydroxyl protecting groups are those of the "hydroxyl protecting group".

The term "leaving group" refers to a molecular fragment that can depart with a pair of electrons in heterolytic bond cleavage. Examples of leaving group are Cl, Br, I, OTs, OTf or OMs.

The term "nucleophile" refers to a chemical species capable of donating an electron pair to another species, during a reaction, to form a chemical bond.

The term "nucleobase" refers to the base moiety of a nucleotide and covers both naturally occuring a well as non-naturally occurring variants. Thus, "nucleobase" covers not only the known purine and pyrimidine heterocycles but also heterocyclic analogues and tautomeres thereof. Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine and 2-chloro-6-aminopurine.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties.

The term "solid support" refers to supports used for the solid phase synthesis, in particular of oligomeric compounds. Examples of solid phase support comprise crosslinked polystyrene (Primer Support 5G or NittoPhaseHL), controlled pore glass (CPG); oxalyl-controlled pore glass, silica-containing particles, such as porous glass beads and silica gel such as that formed by the reaction of trichloro[3-(4-chloromethyl)phenyl]propylsilane and porous glass beads (PORASIL E®). Controlled pore glass is a particular useful solid phase support.

The term "oligonucleotide synthesis activator" refers to a compound capable of activating the reaction of an unprotected nucleoside with an incoming nucleoside phosphoramidite monomer. Examples of such oligonucleotide synthesis activators can be found in X. Wei, *Tetrahedron* 2013, 69, 3615-3637. Examples of oligonucleotide synthesis activators are azole based activators like 1H-tetrazole, 5-nitrophenyl-1H-tetrazole (NPT), 5-ethylthio-1H-tetrazole (ETT), 5-benzylthio-1H-tetrazole (BTT), 5-methylthio-1H-tetrazole (MTT), 5-mercapto-tetrazoles (MCT) and 4,5-dicyanoimidazole (DCI), or acidic salts like pyridinium hydrochloride, imidazoliuim triflate, benzimidazolium triflate, 5-nitrobenzimidazolium triflate, or weak acids such as 2,4-dinitrobenzoic acid or 2,4-dinitrophenol. 5-(3,5-bis(trifluoromethyl)phenyl)-1H-tetrazole is a particularly useful oligonucleotide synthesis activator.

The term "capping" or "capping step" refers to the conversion of hydroxyl or thiohydroxyl groups that have not reacted during the oligonucleotide coupling into a protected hydroxyl or thiohydroxyl group. The capping thus hinders the reaction of said hydroxyl or thiohydroxyl groups in the next coupling steps. The capping step is for example conveniently performed by the reaction with acetic anhydride ($Ac_2O$) or phenoxyacetic anhydride (Pac-anhydride), for example in combination with activators like pyridine and N-methyl-imidazole, for example in THF or acetonitrile. The resulting protected hydroxyl or thiohydroxyl group is for example an acetate or thioacetate group.

The term "sugar modified nucleoside" refers to a nucleoside wherein the sugar is other than DNA or RNA.

The invention thus relates in particular to:

A compound of formula (I) wherein $R^1$ is cyanoethyl or methyl;

A compound of formula (I) wherein $R^2$ and $R^4$ together form —$CH_2O$—;

A compound of formula (I) wherein $R^3$ is diisopropylamino;

A compound of formula (I) wherein $R^5$ is trityl, 4-methoxytrityl, 4,4'-dimethoxytrityl or 4,4',4"-trimethoxytrityl;

A compound of formula (I) wherein $R^5$ is 4,4'-dimethoxytrityl;

A compound of formula (I) wherein each Rp is independently methyl, ethyl or propyl;

A compound of formula (I) wherein the nucleobase is adenine, guanine, cytosine, 5-methyl-cytosine, thymine or uracil;

A compound of formula (I) wherein Nu is (A), (B), (C) or (D)

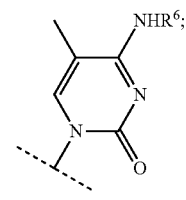

(A)

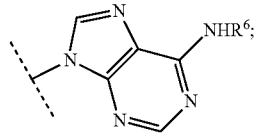

(B)

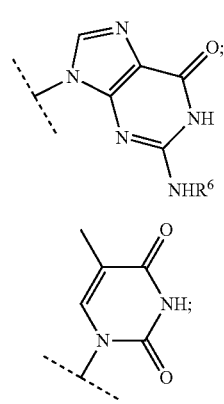
(C)

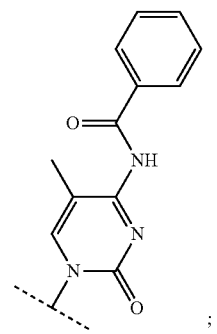
(D)

wherein R⁶ is hydrogen or a protecting group of the amino group to which it is attached;

A compound of formula (I) wherein the protecting group of the amino group is benzoyl, dimethylformamide, acetyl or isobutyryl; and A compound of formula (I) wherein Nu is (A1), (B1) or (C1)

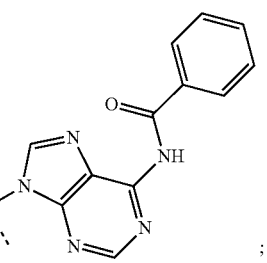
(A1)

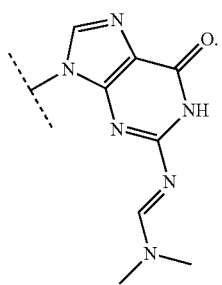
(B1)

(C1)

The invention further relates to a compound of formula (I) selected from

N-{9-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-9H-purin-6-yl}benzamide;

3-[({[1-({[bis(4-methoxyphenyl)(phenyl)methyl]sulfanyl}methyl)-3-(5-methyl-2,4-dioxo-1,2,3,4-tetrahydropyrimidin-1-yl)-2,5-dioxabicyclo[2.2.1]heptan-7-yl]oxy}[bis(propan-2-yl)amino]phosphanyl)oxy]propanenitrile;

N'-{9-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-6-oxo-6,9-dihydro-1H-purin-2-yl}-N,N-dimethylmethanimidamide; and N-{1-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-5-methyl-2-oxo-1,2-dihydropyrimidin-4-yl}benzamide.

The invention further relates in particular to a compound selected from

N-(9-{1-[(benzoylsulfanyl)methyl]-7-hydroxy-2,5-dioxabicyclo[2.2.1]heptan-3-yl}-9H-purin-6-yl)benzamide;

N-{9-[7-hydroxy-1-(sulfanylmethyl)-2,5-dioxabicyclo[2.2.1]heptan-3-yl]-9H-purin-6-yl}benzamide;

N-{9-[1-({[bis(4-methoxyphenyl)(phenyl)methyl]sulfanyl}methyl)-7-hydroxy-2,5-dioxabicyclo[2.2.1]heptan-3-yl]-9H-purin-6-yl}benzamide;

1-[1-({[bis(4-methoxyphenyl)(phenyl)methyl]sulfanyl}methyl)-7-hydroxy-2,5-dioxabicyclo[2.2.1]heptan-3-yl]-5-methyl-1,2,3,4-tetrahydropyrimidine-2,4-dione;

N'-(9-{1-[(benzoylsulfanyl)methyl]-7-hydroxy-2,5-dioxabicyclo[2.2.1]heptan-3-yl}-6-oxo-6,9-dihydro-1H-purin-2-yl)-N,N-dimethylmethanimidamide;

N'-{9-[7-hydroxy-1-(sulfanylmethyl)-2,5-dioxabicyclo[2.2.1]heptan-3-yl]-6-oxo-6,9-dihydro-1H-purin-2-yl}-N,N-dimethylmethanimidamide;

N'-{9-[1-({[bis(4-methoxyphenyl)(phenyl)methyl]sulfanyl}methyl)-7-hydroxy-2,5-dioxabicyclo[2.2.1]heptan-3-yl]-6-oxo-6,9-dihydro-1H-purin-2-yl}-N,N-dimethylmethanimidamide;

N-(1-{1-[(benzoylsulfanyl)methyl]-7-hydroxy-2,5-dioxabicyclo[2.2.1]heptan-3-yl}-5-methyl-2-oxo-1,2-dihydropyrimidin-4-yl)benzamide;

N-{1-[7-hydroxy-1-(sulfanylmethyl)-2,5-dioxabicyclo[2.2.1]heptan-3-yl]-5-methyl-2-oxo-1,2-dihydropyrimidin-4-yl}benzamide and;

N-{1-[1-({[bis(4-methoxyphenyl)(phenyl)methyl]sulfanyl}methyl)-7-hydroxy-2,5-dioxabicyclo[2.2.1]heptan-3-yl]-5-methyl-2-oxo-1,2-dihydropyrimidin-4-yl}benzamide.

The synthesis of the compound of formula (I) can be made for example according to the following schemes. Unless otherwise specified, R¹ to R⁹ and Nu have the meaning as defined above.

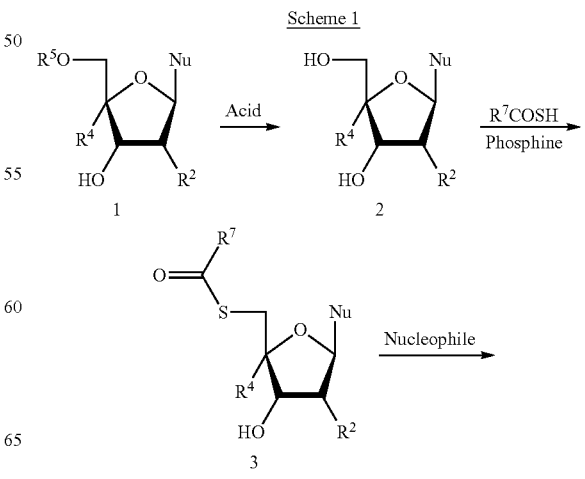

Scheme 1

-continued

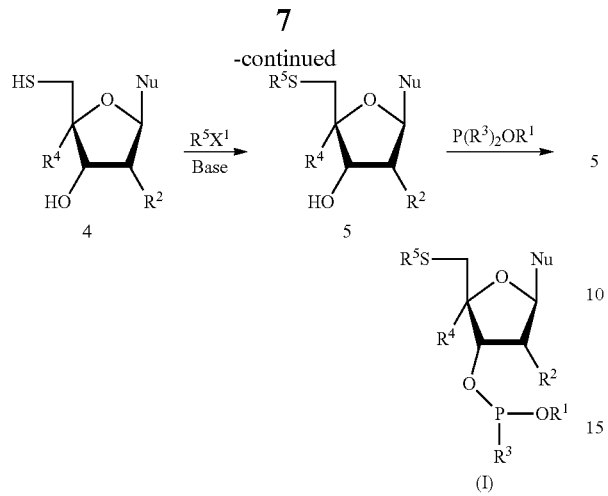

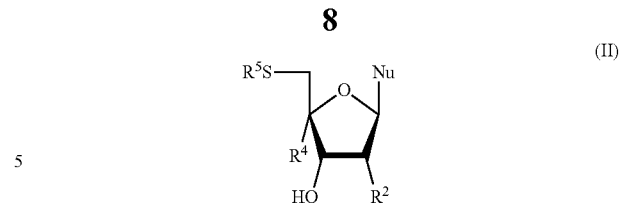

in the presence of $P(R^3)_2OR^1$ and an oligonucleotide synthesis activator wherein $R^1$ to $R^5$ and Nu are as defined above;

A process according to the invention wherein the compound of formula (II) as defined above is obtained by the reaction of a compound of formula (III)

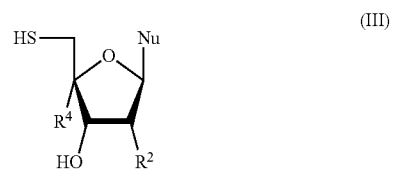

in the presence of $R^5X^1$ and a base, wherein $R^2$, $R^4$, $R^5$ and Nu are as defined above and wherein $X^1$ is a leaving group;

A process according to the invention wherein $X^1$ is Cl, Br, I, OTs, OTf or OMs;

A process according to the invention wherein the compound of formula (III) as defined above is obtained by the hydrolysis of a compound of formula (IV)

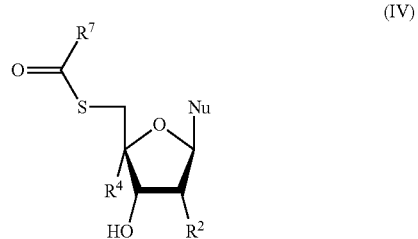

wherein $R^7$ is alkyl, aryl, arylalkyl, substituted aryl or substituted arylalkyl, wherein substituted aryl and substituted arylalkyl are aryl and arylalkyl substituted on the aryl with one to three substitutents independently selected from alkyl, alkoxy and halogen; and wherein $R^2$, $R^4$ and Nu are as defined above;

A process according to the invention wherein the hydrolysis of a compound of formula (IV) is done in the presence of a nucleophile, like e.g. NaOH, KOH, NaOMe, KOMe, methylamine or $NH_3$, in particular NaOH;

A process according to the invention wherein substituted aryl and substituted arylalkyl are aryl and arylalkyl substituted on the aryl with one to three substitutents independently selected from methyl, methoxy, chlorine, bromine and iodine;

A process according to the invention wherein $R^7$ is methyl, ethyl, propyl, isopropyl, benzyl, phenyl, subsituted benzyl or substituted phenyl, wherein substituted phenyl and subsituted benzyl are phenyl and benzyl substituted on the phenyl with one to three substitutents independently selected from methyl, methoxy, chlorine, bromine and iodide;

A process according to the invention wherein $R^7$ is phenyl;

A process according to the invention wherein the compound of formula (IV) as defined above is obtained by the reaction of a compound of formula (V)

Starting from a 5'-protected nucleoside 1 (e.g. 5'-DMT) as well as base protected LNA building blocks (e.g. Nu=protected A, G or C), the corresponding LNA 5'/3' diols 2 are obtained by an acid promoted deprotection. The sulfur is introduced into the 5' position in 3 by means of a Mitsunobu reaction using e.g. thiobenzoic acid as the nucleophile. Subsequent hydrolysis of the resulting thioester gives the free thiol 4, which is then protected with e.g. a DMT group to arrive at 5. Finally, the desired phosphoramidite building block (I) ready for solid phase oligonucleotide synthesis is obtained by phosphitylation of the 3'-hydroxyl group using a suitable phosphoramidite together with a tetrazole derivative as an acidic activator.

Scheme 2

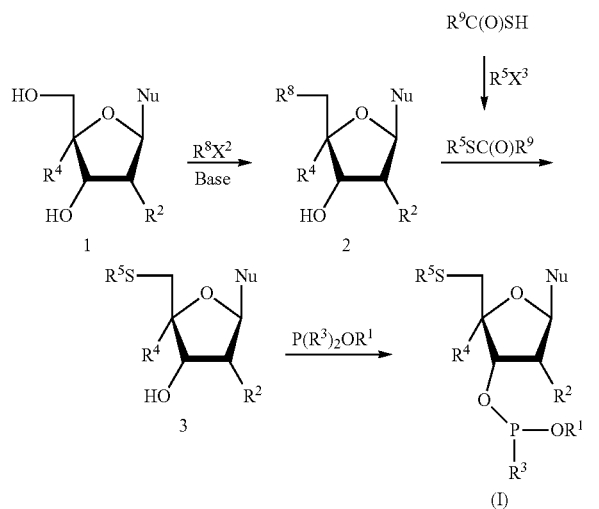

A LNA 5'/3' diol 1 (e.g. Nu=T) is converted to the corresponding 5'-mesylate 2 by the treatment with e.g. methanesulfonyl chloride in the presence of e.g. DMAP in pyridine. This intermediate is then reacted with a protected thioacetate (e.g. DMT-protected thioacetate, obtained by the reaction of e.g. DMT chloride with thioacetic acid) in the presence of base and e.g. sodium methoxide as a nucleophile to arrive at 3. The resulting product is then converted to the desired phosphoramidite building block (I) by phosphitylation of the 3'-hydroxyl group with a phosphoramidite in the presence of an acidic tetrazole activator.

The invention thus also relates to:

A process for the manufacture of a compound of formula (I) comprising the reaction of a compound of formula (II)

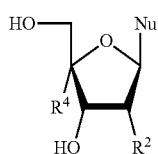

(V)

in the presence of R⁷COSH, a phosphine and a dehydrating agent, wherein $R^2$, $R^4$, $R^7$ and Nu are as defined above;

A process according to the invention wherein the compound of formula (V) is obtained by the removal of the hydroxyl protecting group $R^5$ of a compound of formula (VI)

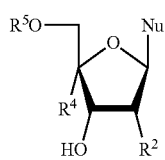

(VI)

wherein $R^5$ is a hydroxyl protecting group, and wherein $R^2$, $R^4$ and Nu are as defined above;

A process according to the invention wherein the compound of formula (II) as defined above is obtained by the reaction of a compound of formula (VII)

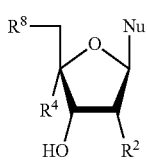

(VII)

in the presence of a base, a nucleophile and a compound of formula (VIII)

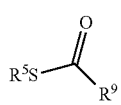

(VIII)

wherein
$R^8$ is a leaving group;
$R^9$ is alkyl; and
$R^2$, $R^4$, $R^5$ and Nu are as defined above;

A process according to the invention wherein $R^9$ is methyl;

A process according to the invention wherein the compound of formula (VII) as defined above is obtained by the reaction of a compound of formula (V) as defined above in the presence of $R^8X^2$ and a non-nucleophilic base, wherein $X^2$ is a leaving group and $R^8$ is a group capable of forming a leaving group together with the 5' hydroxyl oxygen atom of the compound of formula (V);

A process according to the invention wherein $X^2$ is Cl, Br, I, OTs, OTf or OMs;

A process according to the invention wherein the compound of formula (VIII) as defined above is obtained by the reaction of $R^5X^3$ in the presence of $R^9C(O)SH$ wherein $R^5$ and $R^9$ are as defined above and $X^3$ is a leaving group;

A process according to the invention wherein $X^3$ is Cl, Br, I, OTs, OTf or OMs;

A process according to the invention wherein the oligonucleotide synthesis activator is an azole;

A process according to the invention wherein the oligonucleotide synthesis activator is 1H-tetrazole, 5-nitrophenyl-1H-tetrazole (NPT), 5-ethylthio-1H-tetrazole (ETT), 5-benzylthio-1H-tetrazole (BTT), 5-methylthio-1H-tetrazole (MTT), 5-mercapto-tetrazoles (MCT) or 4,5-dicyanoimidazole (DCI);

A process according to the invention wherein the nucleophile used to obtain the compound of formula (II) as defined above is NaOH, KOH, NaOMe, KOMe, methylamine or $NH_3$;

A process according to the invention wherein the nucleophile used to obtain the compound of formula (II) as defined above is NaOMe;

A process according to the invention wherein the dehydrating agent is diethyl azodicarboxylate or diisopropyl azodicarboxylate;

A process according to the invention wherein the dehydrating agent is diethyl azodicarboxylate;

A process according to the invention wherein the phosphine is triphenylphosphine or trimethylphosphine;

A process according to the invention wherein the phosphine is triphenylphosphine;

A process according to the invention wherein the removal of the hydroxyl protecting group $R^5$ of a compound of formula (VI) as defined above is done by the reaction of a compound of formula (VI) in the presence of acid;

A process according to the invention wherein the acid is perchloroacetic acid, acetic acid, chloroacetic acid, dichloroacetic acid or trifluoroacetic acid;

A process according to the invention wherein the acid is perchloroacetic acid;

A compound of formula (II) as defined above;
A compound of formula (III) as defined above; and
A compound of formula (IV) as defined above.

The invention further relates to the use of a compound of the invention for the manufacture of an oligonucleotide.

The invention is also directed to an oligonucleotide comprising a fragment of formula (IX)

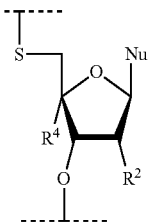

(IX)

wherein $R^2$, $R^4$ and Nu are as defined above.

The invention also relates to a method for the manufacture of an oligonucleotide comprising a fragment of formula (IX) as defined above comprising the following steps:
 (a) Providing a solid support comprising:
  a hydroxyl group;
  a nucleotide comprising a hydroxyl group; or
  an oligonucleotide comprising a hydroxyl group;
 (b) Coupling a compound of the invention, a nucleotide, a locked nucleic acid nucleotide, a 2'-sugar modified nucleotide, a 3'S-DNA or a 3'S-LNA to the hydroxyl group of said solid support;
 (c) Oxidizing or thiooxydizing the product obtained from (b);
 (d) Optionnaly capping unreacted hydroxyl groups of the product obtained from step (c);
 (e) Optionally removing hydroxyl protecting groups or thiohydroxyl protecting groups from the product obtained from step (c) or (d);
 (f) Optionally repeating steps (b) to (e);
 (g) Optionally removing any remaining protecting groups from the product obtained from any one of steps (c) to (f); and
 (h) Optionally cleaving the oligonucleotide from the solid support.

The invention relates in particular to a method for the manufacture of an oligonucleotide comprising a fragment of formula (IX) according to the invention, comprising coupling at least one compound of the invention in a step (b), and in particular a compound of formula (I).

The invention will now be illustrated by the following examples which have no limiting character.

EXAMPLES

Abbreviations:

AcOH=acetic acid, CAS RN=chemical abstracts registration number, DMAP=4-dimethylaminopyridine, DME=dimethoxyethane, DMF=N,N-dimethylformamide, DIPEA=N,N-diisopropylethylamine, dppf=1,1 bis(diphenylphosphino)ferrocene, EI=electron impact, ESI=electrospray ionization, h=hour, HATU=1-[bis(dimethylamino)methylene]-1H-1,2,3-triazolo[4,5-b]pyridinium-3-oxide hexafluorophosphate, HPLC=high performance liquid chromatography, ISP=ion spray positive (mode), ISN=ion spray negative (mode), min=minutes, LAH=lithium aluminium hydride, LiHMDS=lithium bis(trimethylsilyl)amide, MPLC=medium performance liquid chromatography, MS=mass spectrum, PG=protecting group, Pd—C=palladium on activated carbon, PdCl$_2$(dppf)-CH$_2$Cl$_2$=1,1'-bis(diphenylphosphino)ferrocene-palladium (II)dichloride dichloromethane complex, RT=room temperature, S-PHOS=2-dicyclohexylphosphino-2',6'-dimethoxybiphenyl, TFA=trifluroacetic acid, THF=tetrahydrofuran, TMEDA=N,N,N',N'-tetramethylethylenediamine, HBTU=O-Benzotriazole-N,N,N',N'-tetramethyl-uronium-hexafluoro-phosphate, DMEDA=N,N'-dimethylethylenediamine, ACN=acetonitrile, TBAI=tetra butyl ammonium iodile, DME=di methoxy ethane, DEAD=diethyl azodicarboxylate, DMTrCl=4,4'-dimethoxytrityl chloride.

All examples and intermediates were prepared under argon atmosphere if not specified otherwise.

Example 1

N-{9-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-9H-purin-6-yl}benzamide

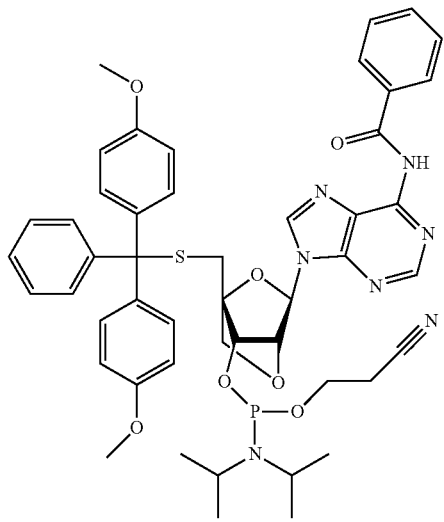 [SMILES: COc1ccc(C(SC[C@@]23COC([C@H](n4cnc5c(NC(=O)c6ccccc6)ncnc54)O2)[C@H]3OP(OCCC#N)N(C(C)C)C(C)C)(c2ccccc2)c2ccc(OC)cc2)cc1]

A solution of 5-ethylmercapto-1H-tetrazole (1.3 g, 9.97 mmol, 0.25 M solution in 38.4 mL dry ACN CAS RN 89797-68-2) was added to a stirred solution of N-{9-[1-({[bis(4-methoxyphenyl)(phenyl)methyl]sulfanyl}methyl)-7-hydroxy-2,5-dioxabicyclo[2.2.1]heptan-3-yl]-9H-purin-6-yl}benzamide (3.5 g, 4.99 mmol) in dry DCM (120 mL) under argon at room temperature followed by addition of 2-cyanoethyl tetraisopropylphosphorodiamodite (3.17 mL, 9.98 mmol, CAS RN 102691-36-1). The reaction mixture was stirred at room temperature for 4 h. Then the reaction mixture was diluted with DCM (300 mL) and poured onto a sat. NaHCO$_3$ solution (100 mL). The organic layer was separated off and the aqueous layer was extracted with DCM (70 mL×2). The combined organic layer was dried over sodium sulfate, filtered and evaporated under reduced pressure. The resulting crude compound was purified by combiflash (10-20% ACN in DCM) to get (2.7 g) impure compound. Using the same protocol another 1 g batch was performed to get 0.6 g impure compound. Using the same protocol another 2.5 g were carried out to get 1 g (pure) compound and 1.5 g impure compound. The impure compound thus obtained from different batches was mixed and repurified to get the title product (3.0 g) which was mixed with pure compound (1 g) to get the title compound (4.0 g, 44%) as a white solid. MS: (ESI): m/z=901.6 [M+H]$^+$.

Example 1.1

N-{9-[7-hydroxy-1-(hydroxymethyl)-2,5-dioxabicyclo[2.2.1]heptan-3-yl]-9H-purin-6-yl}benzamide

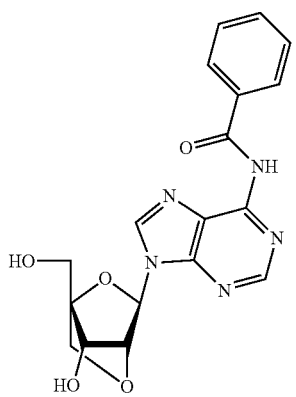

To a solution of Cl$_3$CCOOH (2.98 g, 18.23 mmol, CAS RN 76-03-9) in DCM (150 ml) was added N-[9-(1-{[bis(4-methoxyphenyl)(phenyl)methoxy]methyl}-7-hydroxy-2,5-dioxabicyclo[2.2.1]heptan-3-yl)-9H-purin-6-yl]benzamide (10 g, 14.58 mmol) at 25° C. Then the reaction mixture was stirred for 3 h at 25° C. Volatiles were removed under reduced pressure and the resulting crude was purified by combiflash (10% MeOH in DCM) to get the title product (2) (5 g, 89%) as a white solid. MS: (ESI): m/z=383.8 [M+H]$^+$.

Example 1.2

N-(9-{1-[(benzoylsulfanyl)methyl]-7-hydroxy-2,5-dioxabicyclo[2.2.1]heptan-3-yl}-9H-purin-6-yl)benzamide

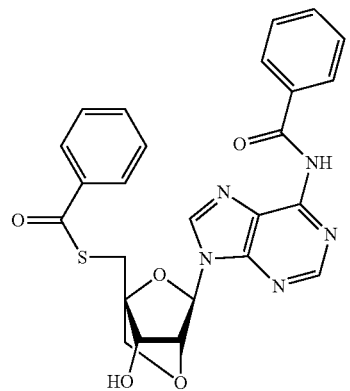 [SMILES: O=C(Nc1ncnc2c1ncn2[C@@H]1O[C@@]2(CSC(=O)c3ccccc3)COC1[C@H]2O)c1ccccc1]

To an ice cooled solution of PPh$_3$ (10.26 g, 39.13 mmol CAS RN 603-35-0) in anhydrous THF (150.0 mL) was added DEAD (6.14 mL, 39.13 mmol, CAS RN 1972-28-7) and the reaction mixture was stirred at 0° C. for 30 min. PhCOSH (4.62 mL, 39.13 mmol, CAS RN 98-91-9) was added drop-wise to the reaction mixture and it was stirred at 0° C. for another 30 min. N-{9-[7-hydroxy-1-(hydroxymethyl)-2,5-dioxabicyclo[2.2.1]heptan-3-yl]-9H-purin-6-yl}benzamide (5.0 g, 13.04 mmol) was added to the stirred reaction mixture at 0° C. for 2 h. The reaction mixture was then stirred at room temperature for 2 h. The reaction mixture was diluted with water (200 mL) and extracted with ethyl acetate (120 mL×3). The combined organic part was washed with NaHCO$_3$ (100 mL), dried over Na$_2$SO$_4$, filtered and evaporated under reduced pressure to get the title product (25 g, crude) as a yellow viscous oil. MS: (ESI): m/z=504.3 [M+H]$^+$.

Example 1.3

N-{9-[7-hydroxy-1-(sulfanylmethyl)-2,5-dioxabicyclo[2.2.1]heptan-3-yl]-9H-purin-6-yl}benzamide

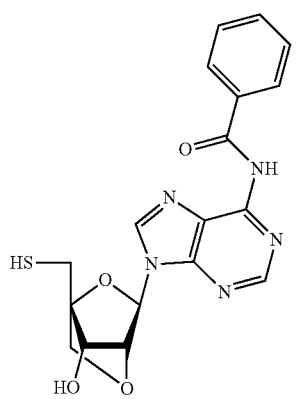 [SMILES: O=C(Nc1ncnc2c1ncn2[C@@H]1O[C@@]2(CS)COC1[C@H]2O)c1ccccc1]

Argon was bubbled through NaOH (0.5 M, 238 mL) as well as solution of THF-MeOH (6:4, 250 mL) for 30 min. N-(9-{1-[(benzoylsulfanyl)methyl]-7-hydroxy-2,5-dioxabicyclo[2.2.1]heptan-3-yl}-9H-purin-6-yl)benzamide (20 g, crude) was dissolved in an argon purged solution of THF-MeOH (6:4, 250 mL) under argon and cooled at 0° C. to −5° C. To this solution was added NaOH solution (0.5 M, 238 mL, 119.16 mmol) and the reaction mixture was stirred at 0° to −5° C. for 30 min. Then a solution of citric acid (30.04 g, 142.98 mmol) was added at 0° C. A saturated NaHCO$_3$ solution (300 mL) was added to the reaction mixture and the mixture was extracted with ethyl acetate (200 mL×3). The combined organic layer was washed with brine, dried over sodium sulfate, filtered and evaporated under reduced pressure to get the title product (20 g, crude) as an off white viscous oil. MS: (ESI): m/z=400.2 [M+H]$^+$.

Example 1.4

N-{9-[1-({[bis(4-methoxyphenyl)(phenyl)methyl]sulfanyl}methyl)-7-hydroxy-2,5-dioxabicyclo[2.2.1]heptan-3-yl]-9H-purin-6-yl}benzamide

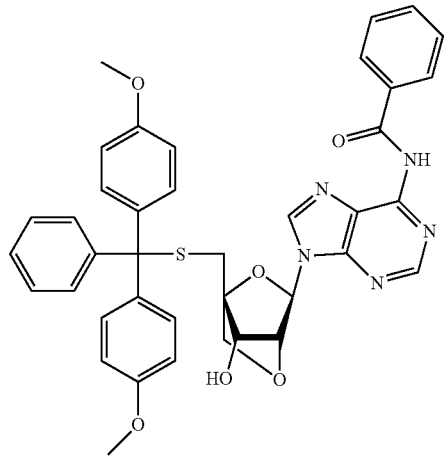 [SMILES: COc1ccc(C(SC[C@@]23COC([C@H](n4cnc5c(NC(=O)c6ccccc6)ncnc54)O2)[C@H]3O)(c2ccccc2)c2ccc(OC)cc2)cc1]

To a solution of N-{9-[7-hydroxy-1-(sulfanylmethyl)-2,5-dioxabicyclo[2.2.1]heptan-3-yl]-9H-purin-6-yl}benzamide (20 g, crude) in anhydrous pyridine (20 mL, argon purged) was added DMTrCl (5.09 g, 15.02 mmol CAS RN 40615-36-9) at 25° C. and the reaction mixture was stirred at 25° C. for 4 h. Volatiles were removed under reduced pressure and the reaction mixture was diluted with DCM (300 mL). The DCM layer was washed with a NaHCO$_3$ solution (100 mL×2) followed by brine (100 mL). The organic layer was dried over Na$_2$SO$_4$, filtered and evaporated under reduced pressure. The resulting crude was purified by combiflash (2% MeOH in DCM containing 0.5% TEA) to get the title product (5 g, 68% over 3 steps) as a pale yellow solid. MS: (ESI): m/z=702.14 [M+H]$^+$.

Example 2

3-[({[1-({[bis(4-methoxyphenyl)(phenyl)methyl]
sulfanyl}methyl)-3-(5-methyl-2,4-dioxo-1,2,3,4-
tetrahydropyrimidin-1-yl)-2,5-dioxabicyclo[2.2.1]
heptan-7-yl]oxy}[bis(propan-2-yl)amino]
phosphanyl)oxy]propanenitrile

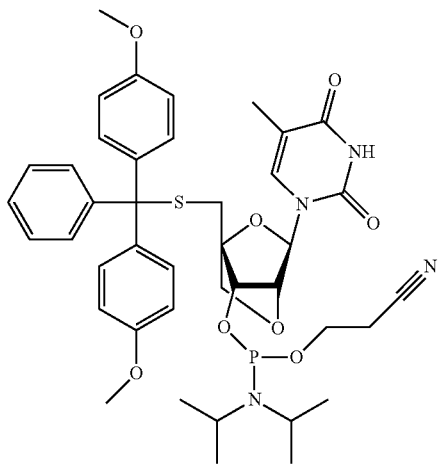 [SMILES: COc1ccc(C(SC[C@@]23COC([C@H](n4cc(C)c(=O)[nH]c4=O)O2)[C@H]3OP(OCCC#N)N(C(C)C)C(C)C)(c2ccccc2)c2ccc(OC)cc2)cc1]

A solution of 5-ethylmercapto-1H-tetrazole (1.77 g, 13.59 mmol, 0.25 M solution in 55.3 mL dry ACN, CAS RN 89797-68-2) and 2-cyanoethyl tetraisopropylphosphorodiamodite (4.31 mL, 13.59 mmol, CAS RN 102691-36-1) were added sequentially to a stirred solution of 1-[1-({[bis(4-methoxyphenyl)(phenyl)methyl]sulfanyl}methyl)-7-hydroxy-2,5-dioxabicyclo[2.2.1]heptan-3-yl]-5-methyl-1,2,3,4-tetrahydropyrimidine-2,4-dione (4.0 g, 6.80 mmol) in dry DCM (150 mL) under argon at 25° C. and the reaction mixture was stirred at 25° C. for 4 h. Then the reaction mixture was diluted with DCM (200 mL) and poured onto a sat. NaHCO$_3$ solution (200 mL). The organic layer was separated off and the aq. layer was extracted with DCM (70 mL×2). The combined organic layer was dried over sodium sulfate, filtered and evaporated under reduced pressure. The resulting crude compound was purified by FCC under argon atmosphere (10-20% ACN in DCM) to get title compound (TM-6) (2.45 g, 46%) as an off white solid. MS: (ESI): m/z=789.4 [M+H]$^+$

Example 2.1

[7-hydroxy-3-(5-methyl-2,4-dioxo-1,2,3,4-tetrahy-
dropyrimidin-1-yl)-2,5-dioxabicyclo[2.2.1]heptan-1-
yl]methyl methanesulfonate

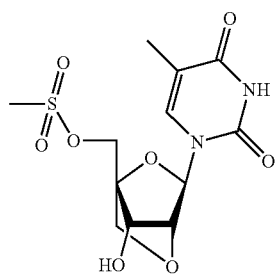 [SMILES: Cc1cn([C@@H]2O[C@@]3(COS(C)(=O)=O)COC2[C@H]3O)c(=O)[nH]c1=O]

To a stirred solution of 1-[7-hydroxy-1-(hydroxymethyl)-2,5-dioxabicyclo[2.2.1]heptan-3-yl]-5-methyl-1,2,3,4-tetrahydropyrimidine-2,4-dione (10 g, 37.00 mmol) in anhydrous pyridine (100.0 mL, CAS RN 110-86-1) were added DMAP (0.452 g, 3.7 mmol) and methane sulfonyl chloride (3.15 mL, 40.71 mmol) at 0° C. to −5° C. sequentially. Then the reaction mixture was stirred at 0° C. for another 3 h. Volatiles were removed under reduced pressure and the resulting crude was purified by combiflash (5% MeOH in DCM) to get the title product (2) (8 g, 62%) as a pale white solid. MS: (ESI): m/z=348.97 [M+H]$^+$.

Example 2.2

1-[1-({[bis(4-methoxyphenyl)(phenyl)methyl]
sulfanyl}methyl)-7-hydroxy-2,5-dioxabicyclo[2.2.1]
heptan-3-yl]-5-methyl-1,2,3,4-tetrahydropyrimidine-
2,4-dione

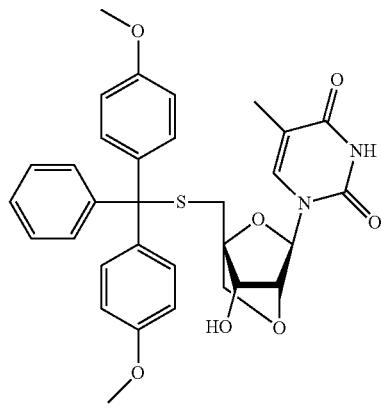 [SMILES: COc1ccc(C(SC[C@@]23COC([C@H](n4cc(C)c(=O)[nH]c4=O)O2)[C@H]3O)(c2ccccc2)c2ccc(OC)cc2)cc1]

To an argon purged solution of 1-{[bis(4-methoxyphenyl)(phenyl)methyl]sulfanyl}ethan-1-one (10.43 g, 27.56 mmol) in dry DMF (80 mL) was added a freshly prepared solution of NaOMe (prepared by adding sodium (0.758 g, 34.45 mmol) to 24 mL of anhydrous methanol followed by the dilution of the resulting solution with DMF (8 mL)) in a drop-wise manner at 25° C. under argon. To the resulting reaction mixture was added a solution of [7-hydroxy-3-(5-methyl-2,4-dioxo-1,2,3,4-tetrahydropyrimidin-1-yl)-2,5-dioxabicyclo[2.2.1]heptan-1-yl]methyl methanesulfonate (4.0 g, 11.48 mmol) and 1,1,3,3 tetramethyl guanidine (3.03 mL, 24.12 mmol, CAS RN 80-70-6) in DMF (32 mL) rapidly. The reaction mixture was stirred at 25° C. for 3 h. Then the reaction mixture was diluted with DCM (400 mL) and washed with a sat. NaHCO$_3$ solution (200 mL). The organic layer was dried over sodium sulfate, filtered and evaporated under reduced pressure. The crude compound was purified by combiflash (ethyl acetate containing 0.5% TEA) to get the title product (3.3 g, 49%) as a pale brown solid. MS: (ESI): m/z=588.89 [M+H]$^+$.

Example 2.3

1-{[bis(4-methoxyphenyl)(phenyl)methyl]sulfanyl}ethan-1-one

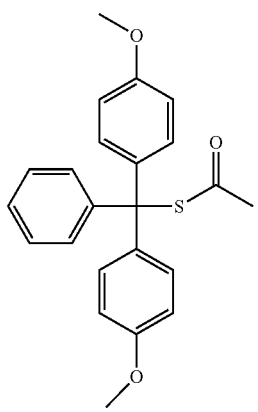 [SMILES: COc1ccc(C(SC(C)=O)(c2ccccc2)c2ccc(OC)cc2)cc1]

To a solution of DMTrCl (10.0 g, 29.51 mmol, CAS RN 40615-36-9) in anhydrous DCM (100.0 mL) was added CH₃COSH (6.24 ml, 88.54 mmol, CAS RN 507-09-5) drop-wise at 0° C. to −5° C. and the reaction mixture was stirred at 0° C. for another 30 min. After completion of reaction, the reaction mixture was neutralized with TEA (12.2 mL, 88.54 mmol) drop-wise at 0° C. Then the reaction mixture was washed with a saturated NaHCO₃ solution (200 mL×2) and brine (100 mL), dried over sodium sulfate, filtered and concentrated under vacuum to get the title compound (11 g, 98%) as pale brown waxy solid.

Example 3

N'-{9-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-6-oxo-6,9-dihydro-1H-purin-2-yl}-N,N-dimethylmethanimidamide

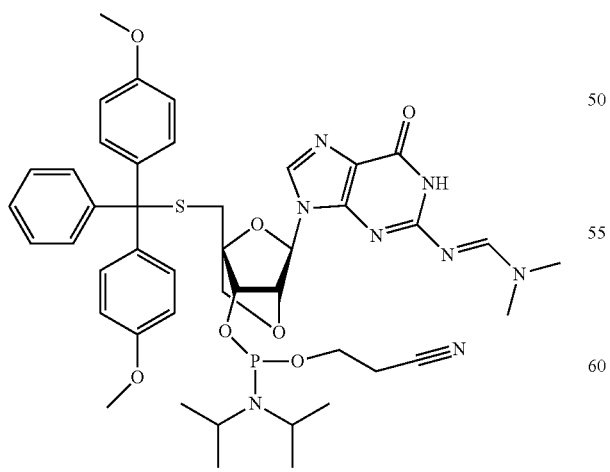

A solution of 5-ethylmercapto-1H-tetrazole (2.65 g, 20.34, 0.25 M solution in 87.5 mL dry ACN, CAS RN 89797-68-2) and 2-cyanoethyl tetraisopropylphosphorodiamodite (6.45 mL, 20.34 mmol, CAS RN 102691-36-1) were added sequentially to a stirred solution of N'-{9-[1-({[bis(4-methoxyphenyl)(phenyl)methyl]sulfanyl}methyl)-7-hydroxy-2,5-dioxabicyclo[2.2.1]heptan-3-yl]-6-oxo-6,9-dihydro-1H-purin-2-yl}-N,N-dimethylmethanimidamide (6.8 g, 10.17 mmol) in dry DCM (200 mL) at 25° C. and the reaction mixture was stirred at 25° C. for 4 h. Then the reaction mixture was diluted with DCM (250 mL) and poured onto a sat. NaHCO₃ solution (200 mL). The organic layer was separated off and the aq. layer was extracted with DCM (2×100 mL). The organic layer was dried over sodium sulfate, filtered and evaporated under reduced pressure. The resultant crude compound was purified by combiflash (90% ACN in DCM) to get title compound (4.2 g, 48%).MS: (ESI): m/z=869.0 [M+H]⁺.

Example 3.1

N'-{9-[7-hydroxy-1-(hydroxymethyl)-2,5-dioxabicyclo[2.2.1]heptan-3-yl]-6-oxo-6,9-dihydro-1H-purin-2-yl}-N,N-dimethylmethanimidamide

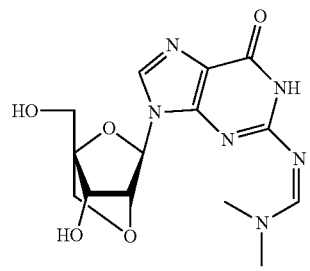

To a solution of 2-amino-9-[7-hydroxy-1-(hydroxymethyl)-2,5-dioxabicyclo[2.2.1]heptan-3-yl]-6,9-dihydro-1H-purin-6-one (10 g, 33.87 mmol) in DMF (100 mL) was added DMF-DMA (9.0 mL, 67.74 mmol, CAS RN 4637-24-5) at 25° C. The mixture was stirred for 4 h at 25° C. Volatiles were removed under reduced pressure and the resultant crude compound was washed with n-hexane (50 mL×3) and dried to get the title compound (13 g, crude) as white solid. MS: (ESI): m/z=350.7 [M+H]⁺.

Example 3.2

N'-(9-{1-[(benzoylsulfanyl)methyl]-7-hydroxy-2,5-dioxabicyclo[2.2.1]heptan-3-yl}-6-oxo-6,9-dihydro-1H-purin-2-yl)-N,N-dimethylmethanimidamide

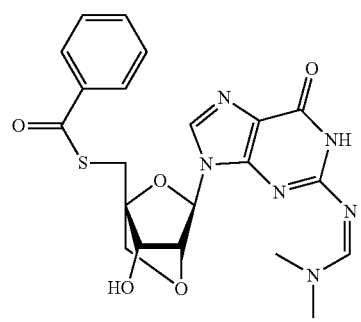 [SMILES: CN(C)/C=N\c1nc2c(ncn2[C@@H]2O[C@@]3(CSC(=O)c4ccccc4)COC2[C@H]3O)c(=O)[nH]1]

To an ice cooled solution of PPh₃ (29.20 g, 111.32 mmol, CAS RN 603-35-0) in anhydrous THF (400 mL) was added DEAD (17.46 mL, 111.32 mmol, CAS RN 1972-28-7) and the reaction mixture was stirred at 0° C. for 30 min. PhCOSH (13.15 mL, 37.11 mmol, CAS RN 98-91-9) was added drop-wise to the reaction mixture and stirring continued at 0° C. for another 30 min. N'-{9-[7-hydroxy-1-(hydroxymethyl)-2,5-dioxabicyclo[2.2.1]heptan-3-yl]-6-oxo-6,9-dihydro-1H-purin-2-yl}-N,N-dimethylmethanimidamide (13 g, crude) was added and stiffing continued at 0° C. for 2 h. Then the reaction mixture was stirred at room temperature for 2 h. Volatiles were removed under reduced pressure and the resultant crude compound was purified by combiflash (5% MeOH in DCM) get the title product (18 g, crude) as a pale yellow solid. MS: (ESI): m/z=470.83 [M+H]⁺.

Example 3.3

N'-{9-[7-hydroxy-1-(sulfanylmethyl)-2,5-dioxabicyclo[2.2.1]heptan-3-yl]-6-oxo-6,9-dihydro-1H-purin-2-yl}-N,N-dimethylmethanimidamide

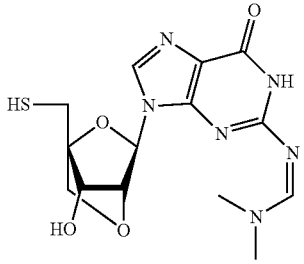 [SMILES: CN(C)/C=N\c1nc2c(ncn2[C@@H]2O[C@@]3(CS)COC2[C@H]3O)c(=O)[nH]1]

To an ice cooled solution of N'-(9-{1-[(benzoylsulfanyl)methyl]-7-hydroxy-2,5-dioxabicyclo[2.2.1]heptan-3-yl}-6-oxo-6,9-dihydro-1H-purin-2-yl)-N,N-dimethylmethanimidamide (18 g, crude) in anhydrous MeOH (300 mL) was added K₂CO₃ (42.30 g, 306.05 mmol, CAS RN 584-08-7) and the reaction mixture was stirred at 0° C. for 2 h and at 25° C. for 2 h. The solvent was evaporated under reduced pressure to get the title compound (60 g, crude) as a pale brown solid. MS: (ESI): m/z=366.6 [M+H]⁺.

Example 3.4

N'-{9-[1-({[bis(4-methoxyphenyl)(phenyl)methyl]sulfanyl}methyl)-7-hydroxy-2,5-dioxabicyclo[2.2.1]heptan-3-yl]-6-oxo-6,9-dihydro-1H-purin-2-yl}-N,N-dimethylmethanimidamide

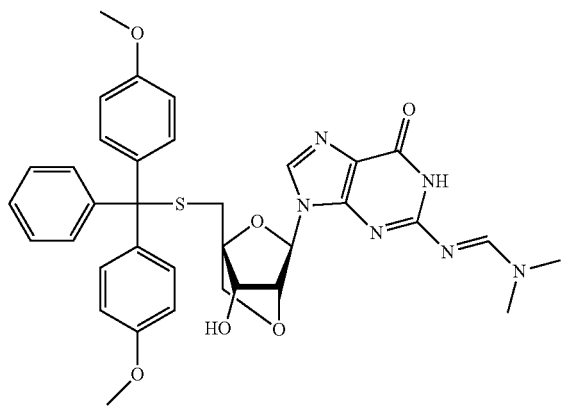 [SMILES: COc1ccc(C(SC[C@@]23COC([C@H](n4cnc5c(=O)[nH]c(/N=C/N(C)C)nc54)O2)[C@H]3O)(c2ccccc2)c2ccc(OC)cc2)cc1]

To a solution of N'-{9-[7-hydroxy-1-(sulfanylmethyl)-2,5-dioxabicyclo[2.2.1]heptan-3-yl]-6-oxo-6,9-dihydro-1H-purin-2-yl}-N,N-dimethylmethanimidamide (60 g, crude) in anhydrous pyridine (80 mL, CAS RN 110-86-1) degassed with argon was added DMTrCl (19.42 g, 57.32 mmol, CAS RN 40615-36-9) at 25° C. and the reaction mixture was stirred at 25° C. for 4 h. Volatiles were removed under reduced pressure and the crude reaction mixture was diluted with water (200 mL). The aq. phase was extracted with ethyl acetate (3×250 mL). The combined organic part was dried over Na₂SO₄, filtered and evaporated under reduced pressure. The resultant crude was purified by combiflash (5% MeOH in DCM containing 0.5% TEA) to get the title product (6.8 g, 30% over 4 steps) as a pale yellow solid. MS: (ESI): m/z=668.6 [M+H]⁺.

Example 4

N-{1-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-5-methyl-2-oxo-1,2-dihydropyrimidin-4-yl}benzamide

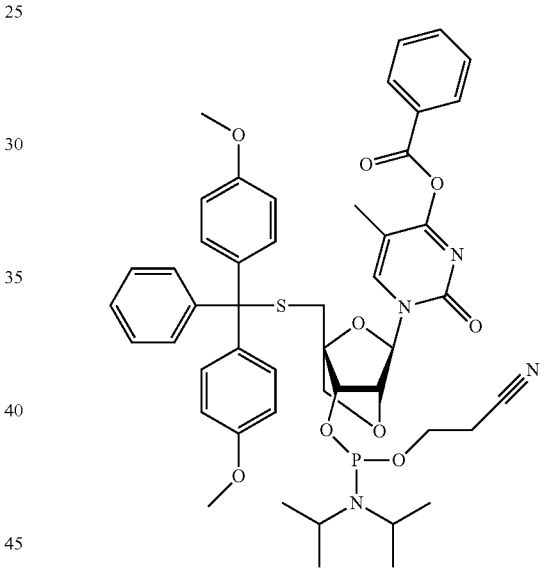

To an ice-cooled solution of N-{1-[1-({[bis(4-methoxyphenyl) (phenyl) methyl] sulfanyl}methyl)-7-hydroxy-2,5-dioxabicyclo[2.2.1]heptan-3-yl]-5-methyl-2-oxo-1,2-dihydropyrimidin-4-yl}benzamide (4.8 g, 6.938) in DCM (50 mL) was added a solution of 5-ethylthio-1H-tetrazole (1.8 g, 13.87 mmol, CAS RN 89797-68-2) in acetonitrile (35 mL) followed by 2-cyanoethyl tetra isopropyl phosphorodiamidite (6.6 mL, 20.18 mmol, CAS RN 102691-36-1) under argon atmosphere at 25° C. and the reaction mixture was stirred for 4 h at 25° C. Then the reaction mixture was poured onto a saturated NaHCO₃ solution (50 mL) and the organic layer was separated off. The aq. layer was extracted with DCM (25 mL×2). The combined organic layer was dried over sodium sulfate, filtered and evaporated under reduced pressure. The resulting crude was purified by column chromatography over silica gel (20% acetonitrile in DCM) to get the title product (3.0 g, 48% yield) as an off white solid. Using the above protocol, another 3 g batch was carried out and mixed with this batch to get the deliverable amount. MS: (ESI): m/z=892.1 [M+H]⁺.

Example 4.1

N-{1-[7-hydroxy-1-(hydroxymethyl)-2,5-dioxabicyclo[2.2.1]heptan-3-yl]-5-methyl-2-oxo-1,2-dihydropyrimidin-4-yl}benzamide

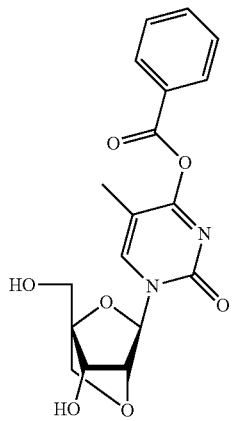 [SMILES: Cc1cn([C@@H]2O[C@@]3(CO)COC2[C@H]3O)c(=O)nc1OC(=O)c1ccccc1]

To a stirred solution of CCl$_3$CO$_2$H (4.5 g, 27.74 mmol, CAS RN 76-03-9) in DCM (100 mL) was added N-[1-(1-{[bis(4-methoxyphenyl)(phenyl)methoxy]methyl}-7-hydroxy-2,5-dioxabicyclo[2.2.1]heptan-3-yl)-5-methyl-2-oxo-1,2-dihydropyrimidin-4-yl]benzamide (15 g, 22.19 mmol) at 25° C. and the reaction mixture was stirred for 2 hours at 25° C. After completion, volatiles were removed under reduced pressure to get the crude residue which was purified by combiflash (10% MeOH in DCM) to get the title product (5.8 g, 69%) as an off-white solid. MS: (ESI): m/z=373.9 [M+H]$^+$.

Examples 4.2

N-(1-{1-[(benzoylsulfanyl)methyl]-7-hydroxy-2,5-dioxabicyclo[2.2.1]heptan-3-yl}-5-methyl-2-oxo-1,2-dihydropyrimidin-4-yl)benzamide

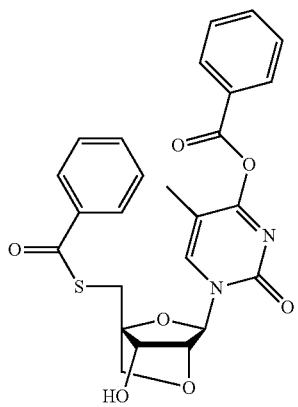 [SMILES: Cc1cn([C@@H]2O[C@@]3(CSC(=O)c4ccccc4)CO[C@H]2C3O)c(=O)nc1OC(=O)c1ccccc1]

To an ice-cooled solution of PPh$_3$ (11.1 g, 42.58 mmol, CAS RN 603-35-0) in dry THF (150 mL) was added DEAD (6.7 mL, 42.58 mmol, CAS RN 1972-28-7) drop-wise and the reaction mixture was stirred at 0° C. under argon atmosphere for 30 min. To this was added PhCOSH (5.03 mL, 42.58 mmol, CAS RN 98-91-9) and stirring continued at 0° C. for 30 min. To the resultant reaction mixture was added N-{1-[7-hydroxy-1-(hydroxymethyl)-2,5-dioxabicyclo[2.2.1]heptan-3-yl]-5-methyl-2-oxo-1,2-dihydropyrimidin-4-yl}benzamide (5.3 g, 14.19 mmol) and stirring continued at 0° C. for 2 h and 2 h at 25° C. Then the reaction mixture was diluted with water (200 mL) and extracted with ethyl acetate (100 mL×3). The combined organic layer was dried over Na$_2$SO$_4$ and evaporated under reduced pressure. The resulting crude was purified by combiflash chromatography (50% ethyl acetate in hexane) to get the title product (7.2 g, crude, contaminated with PPh$_3$O) as an off white solid which was used as such in the next step without further purification MS: (ESI): m/z=493.6 [M+H]$^+$.

Example 4.3

N-{1-[7-hydroxy-1-(sulfanylmethyl)-2,5-dioxabicyclo[2.2.1]heptan-3-yl]-5-methyl-2-oxo-1,2-dihydropyrimidin-4-yl}benzamide

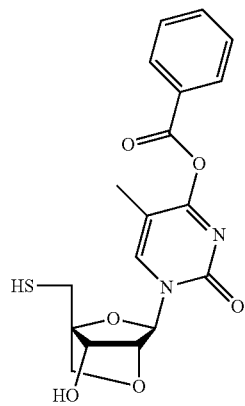 [SMILES: Cc1cn([C@@H]2O[C@@]3(CS)CO[C@H]2C3O)c(=O)nc1OC(=O)c1ccccc1]

To a degassed solution of N-(1-{1-[(benzoylsulfanyl)methyl]-7-hydroxy-2,5-dioxabicyclo[2.2.1]heptan-3-yl}-5-methyl-2-oxo-1,2-dihydropyrimidin-4-yl)benzamide (2.0 g, 4.052 mmol) in THF/MeOH (6:4) (40 mL) under argon was added a solution of NaOH (0.5 M, 24.3 mL) at −5° C. and the reaction mixture was stirred at 0 to −5° C. for 30 min. To the resultant reaction mixture was added a 10% aq. solution of citric acid (30 mL) at 0° C. A saturated sodium bicarbonate solution (50 mL) was added to the reaction mixture and the compound was extracted with ethyl acetate (70 mL×3). The combined organic layer was washed with brine (100 mL×2), dried over sodium sulfate and concentrated under reduced pressure to get the title compound (1.7 g, crude) as a white solid which was used as such in the next step without further purification. MS: (ESI): m/z=390.2 [M+H]$^+$.

Example 4.4

N-{1-[1-({[bis(4-methoxyphenyl)(phenyl)methyl]sulfanyl}methyl)-7-hydroxy-2,5-dioxabicyclo[2.2.1]heptan-3-yl]-5-methyl-2-oxo-1,2-dihydropyrimidin-4-yl}benzamide

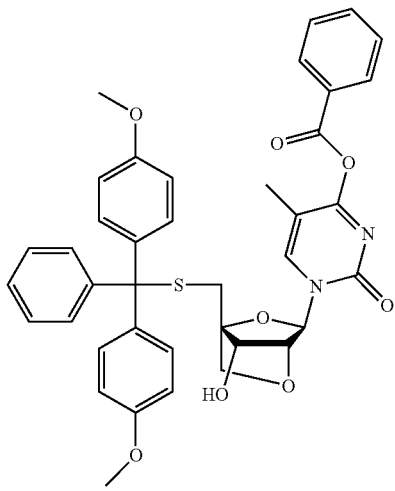 [SMILES: COc1ccc(C(SC[C@]23CO[C@@H](C2O)[C@H](n2cc(C)c(OC(=O)c4ccccc4)nc2=O)O3)(c2ccccc2)c2ccc(OC)cc2)cc1]

To an argon purged solution of crude N-{1-[7-hydroxy-1-(sulfanylmethyl)-2,5-dioxabicyclo[2.2.1]heptan-3-yl]-5-methyl-2-oxo-1,2-dihydropyrimidin-4-yl}benzamide (5.5 g, 14.123 mmol) in dry pyridine (20 mL, CAS RN 110-86-1) was added DMTrCl (7.1 g, 21.18 mmol, CAS RN 40615-36-9) at 25° C. the reaction mixture was stirred at 25° C. for 16 h. Volatiles were removed under reduced pressure and the crude reaction mixture thus obtained was diluted with DCM (200 mL). The organic part was washed with a sat. NaHCO₃ solution (50 mL×2) followed by brine (50 mL×2), dried over sodium sulfate and evaporated under reduced pressure. The resultant crude was purified by combiflash chromatography (35% ethyl acetate in hexane containing 0.5% TEA) to get impure an compound which was repurified by combiflash (30% ethyl acetate/hexane) to get the title compound (4.8 g, 49% yield). MS: (ESI): m/z=690.7 [M+H]⁺.

The invention claimed is:
1. A compound of formula (I)

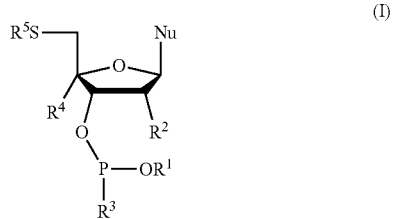

wherein
$R^1$ is a phosphate protecting group;
$R^2$ and $R^4$ together form —CH₂O—, —CH₂NH—, —CH₂S—, —CH₂N(OR$^p$)—, —CHCH₃O—, C(CH₃)₂O, —CH₂C(=CH₂)—, —CHCH₃C(=CH₂)—, —CHCH₃S—, —CH₂NR$^p$—, —CH₂CH₂O—, —CH₂CH₂CH₂O—, —CH₂OCH₂—, —CH(CH₂OCH₃)O—, —CH(CH₂CH₃)O— or —CH₂OCH₂O—;

$R^3$ is dialkylamino;
$R^5$ is a thiohydroxyl protecting group;
each $R^p$ is alkyl; and
Nu is a nucleobase optionally comprising a protected primary amino group.

2. A compound according to claim 1, wherein $R^1$ is cyanoethyl or methyl.

3. A compound according to claim 1, wherein $R^2$ and $R^4$ together form —CH₂O—.

4. A compound according to claim 1, wherein $R^3$ is diisopropylamino.

5. A compound according to claim 1, wherein $R^5$ is trityl, 4-methoxytrityl, 4,4'-dimethoxytrityl or 4,4',4''-trimethoxytrityl.

6. A compound according to claim 1, wherein each Rp is independently methyl, ethyl or propyl.

7. A compound according to claim 1, wherein Nu is adenine, guanine, cytosine, 5-methyl-cytosine, thymine or uracil.

8. A compound according to claim 1, wherein Nu is (A), (B), (C) or (D)

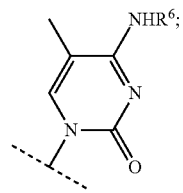 (A)

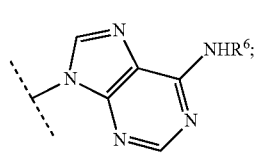 (B)

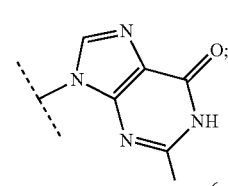 (C)

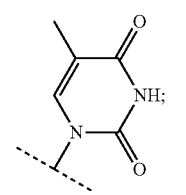 (D)

wherein $R^6$ is hydrogen or a protecting group of the amino group to which it is attached.

9. A compound according to claim 8, wherein the protecting group of the amino group is benzoyl, dimethylformamide, acetyl or isobutyryl.

10. A compound according to claim 1, wherein Nu is (A1), (B1) or (C1)

(A1)

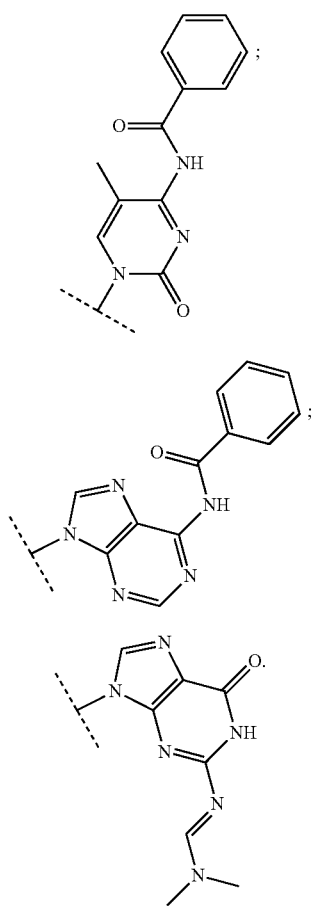

(B1)

(C1)

11. A process for the manufacture of a compound of formula (I), (I)

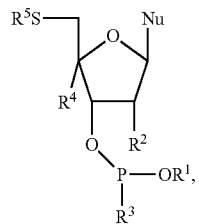

comprising reacting a compound of formula (II)

(II)

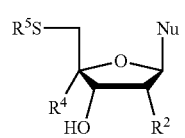

with $P(R^3)_2OR^1$ in the presence of an oligonucleotide synthesis activator, wherein
$R^1$ is a phosphate protecting group;
$R^2$ and $R^4$ together form —CH$_2$O—, —CH$_2$NH—, —CH$_2$S—, —CH$_2$N(OR$^p$)—, —CHCH$_3$O—, C(CH$_3$)$_2$O, —CH$_2$C(=CH$_2$)—, —CHCH$_3$C(=CH$_2$)—, —CHCH$_3$S—, —CH$_2$NR$^p$—, —CH$_2$CH$_2$O—, —CH$_2$CH$_2$CH$_2$O—, —CH$_2$OCH$_2$—, —CH(CH$_2$OCH$_3$)O—, —CH(CH$_2$CH$_3$)O— or —CH$_2$OCH$_2$O—;
$R^3$ is dialkylamino;
$R^5$ is a thiohydroxyl protecting group;
Nu is a nucleobase optionally comprising a protected primary amino group;
and each $R^p$ is independently alkyl.

12. A process according to claim 11, further comprising manufacturing the compound of formula (II) by reacting a compound of formula (III)

(III)

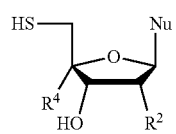

with $R^5X^1$ in the presence of a base, wherein
$R^2$ and $R^4$ together form —CH$_2$O—, —CH$_2$NH—, —CH$_2$S—, —CH$_2$N(OR$^p$)—, —CHCH$_3$O—, C(CH$_3$)$_2$O, —CH$_2$C(=CH$_2$)—, —CHCH$_3$C(=CH$_2$)—, —CHCH$_3$S—, —CH$_2$NR$^p$—, —CH$_2$CH$_2$O—, —CH$_2$CH$_2$CH$_2$O—, —CH$_2$OCH$_2$—, —CH(CH$_2$OCH$_3$)O—, —CH(CH$_2$CH$_3$)O— or —CH$_2$OCH$_2$O—;
$R^3$ is dialkylamino;
$R^5$ is a thiohydroxyl protecting group;
each $R^p$ is alkyl;
Nu is a nucleobase optionally comprising a protected primary amino group
and wherein $X^1$ is a leaving group.

13. A process according to claim 12, further comprising manufacturing the compound of formula (III) by hydrolyzing a compound of formula (IV)

(IV)

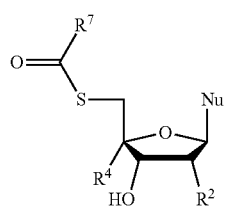

wherein
$R^2$ and $R^4$ together form —CH$_2$O—, —CH$_2$NH—, —CH$_2$S—, —CH$_2$N(OR$^p$)—, —CHCH$_3$O—, C(CH$_3$)$_2$O, —CH$_2$C(=CH$_2$)—, —CHCH$_3$C(=CH$_2$)—, —CHCH$_3$S—, —CH$_2$NR$^p$—, —CH$_2$CH$_2$O—, —CH$_2$CH$_2$CH$_2$O—, —CH$_2$OCH$_2$—, —CH(CH$_2$OCH$_3$)O—, —CH(CH$_2$CH$_3$)O— or —CH$_2$OCH$_2$O—;
$R^7$ is alkyl, aryl, arylalkyl, substituted aryl or substituted arylalkyl, wherein substituted aryl and substituted arylalkyl are aryl and arylalkyl substituted on the aryl with one to three substitutents independently selected from alkyl, alkoxy and halogen.

14. A process according to claim 13, wherein $R^7$ is phenyl.

15. A process according to claim 13, further comprising manufacturing the compound of formula (IV) by reacting a compound of formula (V)

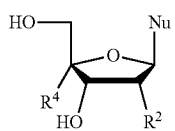
(V)

with R⁷COSH, in the presence of a phosphine and a dehydrating agent, wherein
R⁷ is alkyl, aryl, arylalkyl, substituted aryl or substituted arylalkyl, wherein substituted aryl and substituted arylalkyl are aryl and arylalkyl substituted on the aryl with one to three substitutents independently selected from alkyl, alkoxy and halogen; and
R² and R⁴ together form —CH₂O—, —CH₂NH—, —CH₂S—, —CH₂N(OR^p)—, —CHCH₃O—, C(CH₃)₂O, —CH₂C(=CH₂)—, —CHCH₃C(=CH₂)—, —CHCH₃S—, —CH₂NR^p—, —CH₂CH₂O—, —CH₂CH₂CH₂O—, —CH₂OCH₂—, —CH(CH₂OCH₃)O—, —CH(CH₂CH₃)O— or —CH₂OCH₂O—.

16. A process according to claim 15, further comprising manufacturing the compound of formula (V) by removing the hydroxyl protecting group R⁵ of a compound of formula (VI)

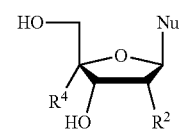
(VI)

wherein R⁵ is a hydroxyl protecting group; and
R² and R⁴ together form —CH₂O—, —CH₂NH—, —CH₂S—, —CH₂N(OR^p)—, —CHCH₃O—, C(CH₃)₂O, —CH₂C(=CH₂)—, —CHCH₃C(=CH₂)—, —CHCH₃S—, —CH₂NR^p—, —CH₂CH₂O—, —CH₂CH₂CH₂O—, —CH₂OCH₂—, —CH(CH₂OCH₃)O—, —CH(CH₂CH₃)O— or —CH₂OCH₂O—.

17. A process according to claim 11, further comprising manufacturing the compound of formula (II) by reacting a compound of formula (VII)

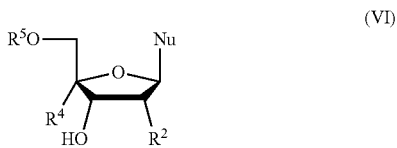
(VII)

and a compound of formula (VIII)

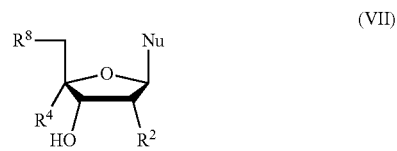
(VIII)

in the presence of a base and a nucleophile wherein
R⁵ is a hydroxyl protecting group;
R² and R⁴ together form —CH₂O—, —CH₂NH—, —CH₂S—, —CH₂N(OR^p)—, —CHCH₃O—, C(CH₃)₂O, —CH₂C(=CH₂)—, —CHCH₃C(=CH₂)—, —CHCH₃S—, —CH₂NR^p—, —CH₂CH₂O—, —CH₂CH₂CH₂O—, —CH₂OCH₂—, —CH(CH₂OCH₃)O—, —CH(CH₂CH₃)O— or —CH₂OCH₂O—;
R⁸ is a leaving group; and
R⁹ is alkyl.

18. A process according to claim 17, further comprising manufacturing the compound of formula (VII) by reacting a compound of formula (V)

(V)

with R⁸X² in the presence of a non-nucleophilic base, wherein X² is a leaving group and R⁸ is a group capable of forming a leaving group together with the 5' hydroxyl oxygen atom of the compound of formula (V).

19. A process according to claim 17, further comprising manufacturing the compound of formula (VIII) by reacting R⁵X³ with R⁹C(O)SH, wherein
X³ is a leaving group and R⁹ is alkyl.

20. A process according to claim 11, wherein the oligonucleotide synthesis activator is an azole.

21. A process according to claim 11, wherein the oligonucleotide synthesis activator is selected from the group consisting of: 1H-tetrazole, 5-nitrophenyl-1H-tetrazole (NPT), 5-ethylthio-1H-tetrazole (ETT), 5-benzylthio-1H-tetrazole (BTT), 5-methylthio-1H-tetrazole (MTT), 5-mercapto-tetrazoles (MCT) and 4,5-dicyanoimidazole (DCI).

22. A process according to claim 17, wherein the nucleophile is selected from the group consisting of: NaOH, KOH, NaOMe, KOMe, methylamine and NH₃.

23. A process according to claim 15, wherein the dehydrating agent is diethyl azodicarboxylate or diisopropyl azodicarboxylate.

24. A process according to claim 12, wherein the phosphine is triphenylphosphine or trimethylphosphine.

25. A process according to claim 16, wherein the removal of the hydroxyl protecting group R⁵ of a compound of formula (VI) is done by the reaction of a compound of formula (VI) in the presence of acid.

26. A process according to claim 25, wherein the acid is selected from the group consisting of: perchloroacetic acid, acetic acid, chloroacetic acid, dichloroacetic acid or trifluoroacetic acid.

27. A compound according to claim 1 selected from
N-{9-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-9H-purin-6-yl}benzamide;
3-[({[1-({[bis(4-methoxyphenyl)(phenyl)methyl]sulfanyl}methyl)-3-(5-methyl-2,4-dioxo-1,2,3,4-tetrahydropyrimidin-1-yl)-2,5-dioxabicyclo[2.2.1]heptan-7-yl]oxy}[bis(propan-2-yl)amino]phosphanyl)oxy]propanenitrile;
N'-{9-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-6-oxo-6,9-dihydro-1H-purin-2-yl}-N,N-dimethylmethanimidamide; and N-{1-[1-({[bis(4-methoxyphenyl)(phenyl)methyl]sulfanyl}methyl)-7-({[bis(propan-2-yl)amino](2-cyanoethoxy)phosphanyl}oxy)-2,5-dioxabicyclo[2.2.1]heptan-3-yl]-5-methyl-2-oxo-1,2-dihydropyrimidin-4-yl}benzamide.

28. A compound selected from
N-(9-{1-[(benzoylsulfanyl)methyl]-7-hydroxy-2,5-dioxabicyclo[2.2.1]heptan-3-yl}-9H-purin-6-yl)benzamide;
N-{9-[7-hydroxy-1-(sulfanylmethyl)-2,5-dioxabicyclo[2.2.1]heptan-3-yl]-9H-purin-6-yl}benzamide;
N-{9-[1-({[bis(4-methoxyphenyl)(phenyl)methyl]sulfanyl}methyl)-7-hydroxy-2,5-dioxabicyclo[2.2.1]heptan-3-yl]-9H-purin-6-yl}benzamide;
1-[1-({[bis(4-methoxyphenyl)(phenyl)methyl]sulfanyl}methyl)-7-hydroxy-2,5-dioxabicyclo[2.2.1]heptan-3-yl]-5-methyl-1,2,3,4-tetrahydropyrimidine-2,4-dione;
N'-(9-{1-[(benzoylsulfanyl)methyl]-7-hydroxy-2,5-dioxabicyclo[2.2.1]heptan-3-yl}-6-oxo-6,9-dihydro-1H-purin-2-yl)-N,N-dimethylmethanimidamide;
N'-{9-[7-hydroxy-1-(sulfanylmethyl)-2,5-dioxabicyclo[2.2.1]heptan-3-yl]-6-oxo-6,9-dihydro-1H-purin-2-yl}-N,N-dimethylmethanimidamide;
N'-{9-[1-({[bis(4-methoxyphenyl)(phenyl)methyl]sulfanyl}methyl)-7-hydroxy-2,5-dioxabicyclo[2.2.1]heptan-3-yl]-6-oxo-6,9-dihydro-1H-purin-2-yl}-N,N-dimethylmethanimidamide;
N-(1-{1-[(benzoylsulfanyl)methyl]-7-hydroxy-2,5-dioxabicyclo[2.2.1]heptan-3-yl}-5-methyl-2-oxo-1,2-dihydropyrimidin-4-yl)benzamide;
N-{1-[7-hydroxy-1-(sulfanylmethyl)-2,5-dioxabicyclo[2.2.1]heptan-3-yl]-5-methyl-2-oxo-1,2-dihydropyrimidin-4-yl}benzamide and;
N-{1-[1-({[bis(4-methoxyphenyl)(phenyl)methyl]sulfanyl}methyl)-7-hydroxy-2,5-dioxabicyclo[2.2.1]heptan-3-yl]-5-methyl-2-oxo-1,2-dihydropyrimidin-4-yl}benzamide.

29. An oligonucleotide comprising a fragment of formula (IX)

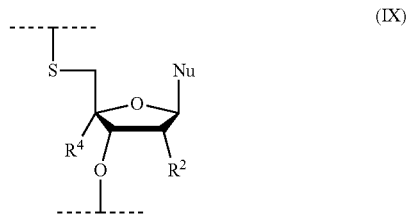

wherein
$R^2$ and $R^4$ together form —$CH_2NH$—, —$CH_2S$—, —$CH_2N(OR^p)$—, —$CHCH_3O$—, —$C(CH_3)_2O$—, —$CH_2C(=CH_2)$—, —$CHCH_3C(=CH_2)$—, —$CHCH_3S$—, —$CH_2NR^p$—, —$CH_2CH_2O$—, —$CH_2CH_2CH_2O$—, —$CH_2OCH_2$—, —$CH(CH_2OCH_3)O$—, —$CH(CH_2CH_3)O$— or —$CH_2OCH_2O$—; wherein each $R^p$ is alkyl; and
Nu is a nucleobase optionally comprising a protected primary amino group.

30. A method for the manufacture of an oligonucleotide comprising a fragment of formula (IX) as defined in claim 29 comprising the following steps:
(a) Providing a solid support comprising:
a hydroxyl group;
a nucleotide comprising a hydroxyl group; or
an oligonucleotide comprising a hydroxyl group;
(b) coupling a compound selected from the group consisting of:
a compound of formula (I)

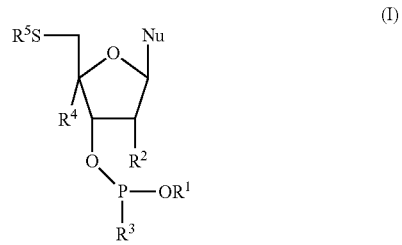

wherein
$R^1$ is a phosphate protecting group;
$R^2$ and $R^4$ together form —$CH_2O$—, —$CH_2NH$—, —$CH_2S$—, —$CH_2N(OR^p)$—, —$CHCH_3O$—, —$C(CH_3)_2O$—, —$CH_2C(=CH_2)$—, —$CHCH_3C(=CH_2)$—, —$CHCH_3S$—, —$CH_2NR^p$—, —$CH_2CH_2O$—, —$CH_2CH_2CH_2O$—, —$CH_2OCH_2$—, —$CH(CH_2OCH_3)O$—, —$CH(CH_2CH_3)O$— or —$CH_2OCH_2O$—;
$R^3$ is dialkylamino;
$R^5$ is a thiohydroxyl protecting group;
each $R^p$ is alkyl; and
Nu is a nucleobase optionally comprising a protected primary amino group, a nucleotide, a locked nucleic acid nucleotide, a 2'-sugar modified nucleotide, a 3'S-DNA or a 3'S-LNA to the hydroxyl group of said solid support;
(c) oxidizing or thiooxydizing the product obtained from (b);
(d) optionally capping unreacted hydroxyl groups of the product obtained from step (c);
(e) optionally removing hydroxyl protecting groups or thiohydroxyl protecting groups from the product obtained from step (c) or (d);
(f) optionally repeating steps (b) to (e);
(g) optionally removing any remaining protecting groups from the product obtained from any one of steps (c) to (f); and
(h) optionally cleaving the oligonucleotide from the solid support.

* * * * *